US011266323B2

(12) United States Patent
Han et al.

(10) Patent No.: US 11,266,323 B2
(45) Date of Patent: Mar. 8, 2022

(54) SKIN MEASURING APPARATUS FOR MEASURING SKIN MOISTURE LEVEL USING VOLTAGE APPLICATION ELECTRODE AND CURRENT DETECTION ELECTRODE

(71) Applicant: GPOWER INC., Seoul (KR)

(72) Inventors: Chang Hee Han, Gyeonggi-do (KR); Deug Ki Lee, Seoul (KR)

(73) Assignee: GPOWER INC., Seoul (KR)

( * ) Notice: Subject to any disclaimer, the term of this patent is extended or adjusted under 35 U.S.C. 154(b) by 812 days.

(21) Appl. No.: 16/072,806

(22) PCT Filed: Apr. 4, 2017

(86) PCT No.: PCT/KR2017/003694
§ 371 (c)(1),
(2) Date: Jul. 25, 2018

(87) PCT Pub. No.: WO2018/186506
PCT Pub. Date: Oct. 11, 2018

(65) Prior Publication Data
US 2021/0169364 A1 Jun. 10, 2021

(51) Int. Cl.
*A61B 5/0537* (2021.01)
*G16H 50/30* (2018.01)
(Continued)

(52) U.S. Cl.
CPC ............ *A61B 5/0537* (2013.01); *A61B 5/443* (2013.01); *A61B 5/4875* (2013.01);
(Continued)

(58) Field of Classification Search
CPC ..... A61B 5/053; A61B 5/0531; A61B 5/7225; A61B 5/0537; A61B 5/4266; A61B 5/443; A61B 5/4875; A61B 5/14517
(Continued)

(56) References Cited

U.S. PATENT DOCUMENTS 4,814,696 A * 3/1989 Kern ..................... G01R 21/001
324/142
5,680,108 A * 10/1997 Daniell .............. A47G 19/2227
250/215
(Continued)

FOREIGN PATENT DOCUMENTS

JP 2006-334415 A 12/2006
JP 2010-172543 A 8/2010
(Continued)

OTHER PUBLICATIONS

Visser, C. A Micro Approach to Quantitative Dehydration Sensor Development (Thesis). Mar. 2015, Stellenbosch University. (Year: 2015).*

(Continued)

*Primary Examiner* — Jason M Sims
*Assistant Examiner* — James Stewart Stambaugh, III
(74) *Attorney, Agent, or Firm* — The PL Law Group, PLLC

(57) ABSTRACT

A skin measuring apparatus measures a skin moisture level using a voltage application electrode and a current detection electrode. The skin measuring apparatus includes an electrode driving module applying sinusoidal wave voltage to skin of a user through the voltage application electrode so that an amount of current is output from the skin through the current detection electrode, a signal detecting unit detecting the amount of current from the skin through the current detection electrode to calculate at least one of an impedance signal and an admittance signal, and a skin information determination unit analyzing the at least one of the impedance signal and the admittance signal to calculate the skin moisture level and a sweat production rate of the user, thereby analyzing the skin moisture level and the sweat generation rate more precisely without distortion.

8 Claims, 5 Drawing Sheets

(51) Int. Cl.
*G16H 40/63* (2018.01)
*A61B 5/00* (2006.01)

(52) U.S. Cl.
CPC .......... *A61B 5/7225* (2013.01); *G16H 40/63* (2018.01); *G16H 50/30* (2018.01)

(58) Field of Classification Search
USPC ........................................ 600/306, 346, 547
See application file for complete search history.

(56) References Cited

U.S. PATENT DOCUMENTS

| | | | | |
|---|---|---|---|---|
| 7,581,434 | B1* | 9/2009 | Discenzo | G01N 33/2888 73/53.01 |
| 2004/0126814 | A1* | 7/2004 | Singh | C08F 8/00 435/7.1 |
| 2006/0281981 | A1* | 12/2006 | Jang | A61B 5/442 600/306 |
| 2008/0045816 | A1 | 2/2008 | Jang et al. | |
| 2008/0091091 | A1* | 4/2008 | Jang | A61B 5/442 600/306 |
| 2010/0179403 | A1* | 7/2010 | Martinsen | A61B 5/4266 600/346 |
| 2011/0144523 | A1* | 6/2011 | Storm | A61B 5/4821 600/547 |

FOREIGN PATENT DOCUMENTS

| | | |
|---|---|---|
| KR | 10-2008-0016339 A | 2/2008 |
| KR | 10-2011-0085066 A | 7/2011 |
| KR | 10-2014-0076852 A | 6/2014 |
| WO | WO 2011/016407 A1 | 2/2011 |

OTHER PUBLICATIONS

Office action dated Jul. 29, 2020 from China Patent Office in a counterpart China Patent Application No. 201780008383.9 (English translation is also submitted herewith).

* cited by examiner

SKIN MEASURING APPARATUS FOR MEASURING SKIN MOISTURE LEVEL USING VOLTAGE APPLICATION ELECTRODE AND CURRENT DETECTION ELECTRODE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/003694, filed Apr. 4, 2017, the entire contents of which are incorporated herein by reference.

TECHNICAL FIELD

The present invention relates to a skin measuring apparatus and, more particularly, to a skin measuring apparatus for measuring a skin moisture level using a voltage application electrode and a current detection electrode, which is capable of more precisely analyzing a skin moisture level and a sweat production rate of a user without distortion even with a simplified structure, by applying sinusoidal wave voltage to the skin of the user through a voltage application electrode and detecting an amount of current from the skin through a current detection electrode.

BACKGROUND ART

The skin exists in the outermost part of a human body and performs important functions such as preventing invasion of bacteria and harmful substances from the outside, waterproofing, maintenance of internal body temperature, and the like. The most important factor in maintaining the basic function of this skin is moisture content of stratum corneum. Only when the appropriate moisture content of the stratum corneum is maintained, it is possible to prevent intrusion of harmful substances from the outside and to suppress an amount of water evaporation from the inside, and thus enable primary functions of the skin to be performed. Therefore, it may be noted that moisturizing is the foundation of skin care and the most important thing is to know and manage his/her own skin moisture level.

Conventional methods for measuring skin water content include an electrical measurement method, an optical measurement method, a method using MRI, and the like. Among them, an electric method has been mainly used, particularly, a method of measuring susceptance that is an AC component of the admittance component with a three-electrode scheme of a reference electrode (R electrode), a current carrying electrode (C electrode), and a measuring electrode (M electrode).

In Korean Patent Application Publication No. 10-2008-0016339 (published Feb. 21, 2008), a technique has been proposed that applies a predefined voltage to the skin of the user with an R, C, and M electrode scheme, detects a current signal flowing through the skin of the user, and measures skin water content and activity of sweat duct of the user using the detected current signal and a predefined phase signal.

However, the methods of measuring the skin water content by the R, C, and M electrode scheme including the conventional technique proposed in No. 10-2008-0016339 have a problem that the C electrode and the R electrode have to be in contact with the skin at the same time. When the R electrode first is in contact with the skin in the state where the C electrode is not in contact with the skin, the sinusoidal wave applied from the C electrode to the skin may be distorted so that the skin impedance cannot be measured and, even though it is measured, the result is distorted. In addition, since all the R, C, and M electrodes have to be in stable contact with the skin during skin impedance measurement, there is a problem that a measurement error occurs due to the movement of a user.

On the other hand, with respect to the method of measuring skin water content using the R, C, and M electrode scheme, the sinusoidal wave applied from the C electrode to the skin changes in phase and amplitude by a negative feedback structure in which the skin impedance is connected to the R, C, M electrodes, whereby a problem arises that an impedance measurement value is distorted by such change in phase and amplitude. Specifically, simulating the change in the phase and amplitude of a sinusoidal wave applied from the C electrode to the skin by the negative feedback structure in which the R, C, and M electrodes are connected to the skin impedance, it may be confirmed that the sinusoidal wave applied from the C electrode to the actual skin changes in the phase and amplitude (the lower waveform shown in FIG. 1), compared with a sine wave applying a signal (the upper waveform shown in FIG. 1), as shown in FIG. 1. In particular, it is very difficult to calibrate the impedance measurement value because the impedance of the skin changes in real time according to the structure and condition of skin and is directly affected by the degree of change in the applied sinusoidal wave.

As a problem occurs that the impedance measurement value is distorted due to distortion of the sinusoidal wave or voltage applied to the skin is increased, research for resolving and compensating the problem have been progressed. However, a circuit structure is added and thus becomes complicated, and manufacturing costs are greatly increased, whereby the efficiency thereof is deteriorated.

SUMMARY

Accordingly, the present invention has been made keeping in mind the above problems occurring in the related art, and an object of the present invention is to provide an skin measuring apparatus for measuring a skin moisture level using a voltage application electrode and a current detection electrode, which is capable of more precisely analyzing the skin moisture level and the sweat production rate of the user without distortion even with a simplified structure, by applying sinusoidal wave voltage to the skin of the user through the voltage application electrode and detecting an amount of current from the skin through the current detection electrode.

In order to accomplish the above object, according to an embodiment, the present invention provides a skin measuring apparatus for measuring a skin moisture level using a voltage application electrode and a current detection electrode, the apparatus including: an electrode driving module applying sinusoidal wave voltage to skin of a user through the voltage application electrode so that an amount of current is output from the skin through the current detection electrode; a signal detecting unit detecting the amount of current from the skin through the current detection electrode to calculate at least one of an impedance signal and an admittance signal; and a skin information determination unit analyzing the at least one of the impedance signal and the admittance signal to calculate the skin moisture level and a sweat production rate of the user.

The skin measuring apparatus for measuring a skin moisture level using a voltage application electrode and a current detection electrode according to the present invention has an advantage that it is possible to more precisely analyze a skin moisture level and a sweat production rate of a user without distortion even with a simplified structure by applying sinusoidal wave voltage to the skin of the user through a voltage application electrode and detecting an amount of current from the skin through a current detection electrode.

Particularly, it is possible to use a simplified structure using only two electrodes for a voltage application electrode that applies applying sinusoidal wave voltage to the skin of the user and a current detection electrode that detects an amount of current flowing through the skin.

In addition, the operational amplifier that is provided in the electrode driving module to output the sinusoidal wave voltage is configured such that the sinusoidal wave voltage outputted to an output terminal is feedback and input to the negative signal input terminal (−) thereof, whereby it is possible to prevent distortion due to skin impedance, and thus improve the accuracy when measuring the skin impedance.

In addition, the accuracy of detection of the impedance or the admittance signal may be further improved by compensating for phase delay occurring in the signal detecting unit that detects the impedance or the admittance signal by sharing and using the sinusoidal wave voltage applied to the skin.

DETAILED DESCRIPTION

Hereinafter, some embodiments of the present invention will be described in detail with reference to exemplary drawings.

Figure 2:
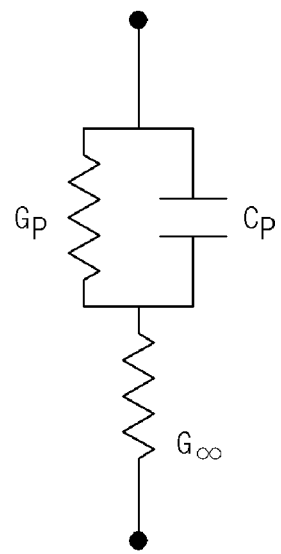
FIG. 2 is an equivalent circuit diagram electrically modeling the skin structure.
Figure 3:
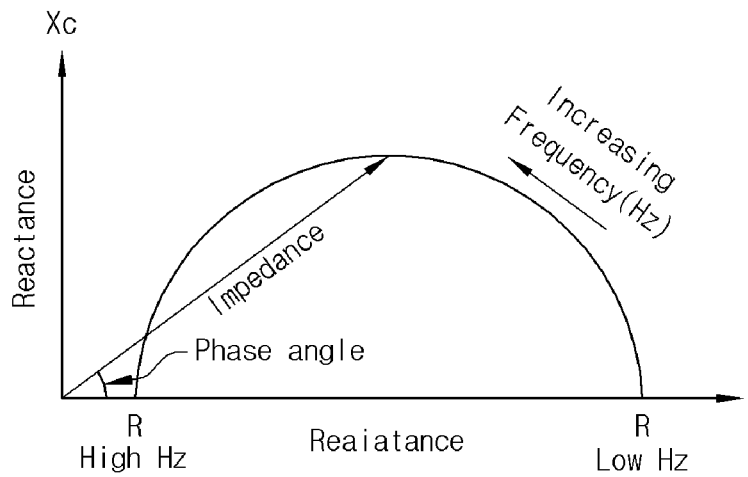
FIG. 3 is a graph showing impedance characteristics according to frequency applied to the skin.

FIG. 2 is an equivalent circuit diagram electrically modeling the skin structure, and FIG. 3 is a graph showing impedance characteristics according to frequency applied to the skin.

First, in order to electrically measure the skin moisture level, the physiological structure of the skin has to be electrically modeled. When the skin structure is modeled electrically with respect to parameters of the Cole equation, the modeling may be represented as shown in FIG. 2. Here, conductance Gp and capacitance Cp are variable with respect to the frequency, and are elements that are based on a dead skin cell. Impedance $Z\infty$ of deep tissue containing the granular layer is still much smaller than impedance of dead skin cell within the frequency range below 10 kHz and is obtained from an estimated value of infinite frequency $f\infty$ in the impedance vector distribution.

Referring to FIG. 2, impedance is an element that interferes with the flow of alternating current. The skin impedance depends on frequency and interferes with the electrical flow of the alternating current. In particular, as proposed in Equation 1 below, the impedance Z may be obtained by summing two vectors of resistance G and reactance Xc measured at a specific frequency.

$$Z=\sqrt{(R^2+X_c^2)} \quad \text{[Equation 1]}$$

The low-frequency current may not pass through the cell due to the inherent capacitive characteristics of cell membrane of the skin, and the high-frequency currents may pass through the cell membrane to allow the impedance to be specified as sum of intracellular fluid substance and extracellular fluid substance. Accordingly, the current at a low frequency below 10 kHz flows only in the skin so that the skin impedance is determined by the stratum corneum having dominant resistance component, and the current at a frequency above 10 kHz penetrates through the skin to reach the lower body tissue so that the skin impedance is not reflected.

Figure 1:
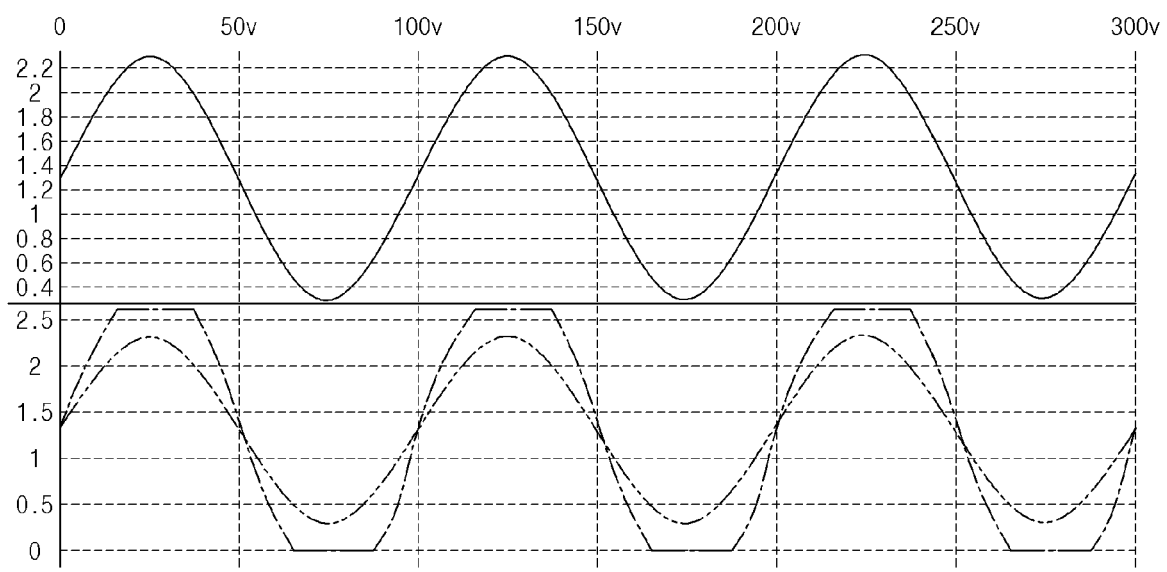
FIG. 1 is a simulation graph showing the degree of change in phase and amplitude of a sinusoidal wave according to the related art.

According to the present invention, in order to measure the skin impedance of the user on a basis of the skin model shown in FIG. 1, a sinusoidal wave AC voltage is applied to the skin of the user and then the current flowing at that time is measured, whereby the skin impedance, that is skin DC resistance and capacitance, is measured and the skin condition such as skin moisture level is measured and analyzed from the measured impedance.

Figure 4:
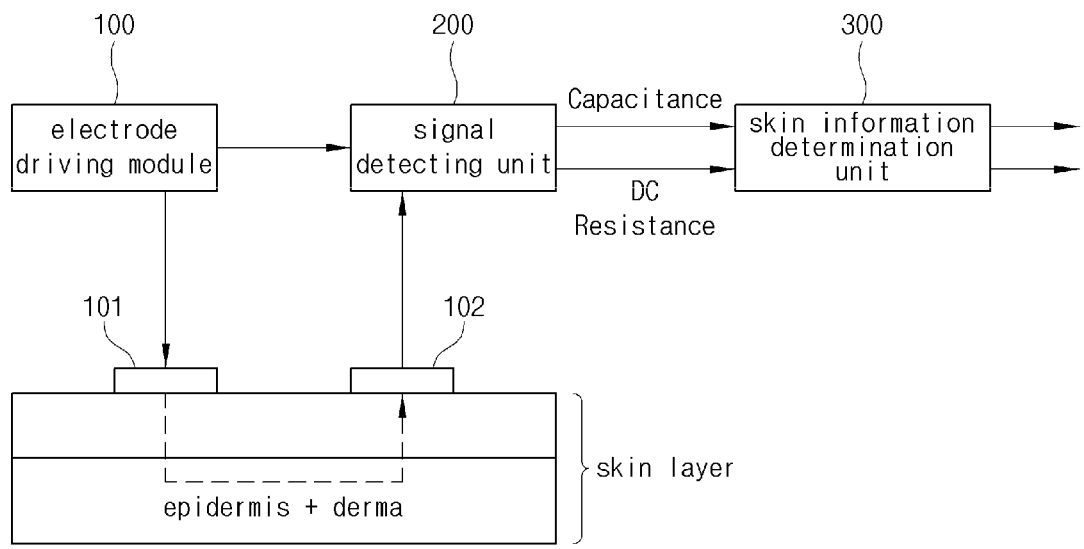
FIG. 4 is a block diagram illustrating a skin measuring apparatus for measuring the skin moisture level using a voltage application electrode and a current detection electrode according to an embodiment of the present invention.

FIG. 4 is a block diagram illustrating an apparatus for measuring the skin moisture level using a voltage application electrode and a current detection electrode according to an embodiment of the present invention.

The skin measuring apparatus shown in FIG. 4 is configured to include an electrode driving module 100 for applying a sinusoidal wave voltage to the skin of the user through a voltage application electrode 101, signal detecting unit 200 for calculating at least one of a skin impedance signal and a skin admittance signal, and a skin information determination unit 300 for calculating the skin moisture level and the sweat production rate.

Specifically, the electrode driving module 100 applies a sinusoidal wave voltage to the skin of the user through the voltage application electrode 101 so that the amount of current may be output from the skin through the current detection electrode 102. The electrode driving module 100 generates a sinusoidal current to be operationally amplified and changed into the voltage having the same phase or an inversion phase as the sinusoidal wave and then applies the resulting sinusoidal wave voltage to the skin of the user through the voltage application electrode 101. Accordingly, when the sinusoidal wave voltage applied to the skin of the user through the voltage application electrode 101 reacts with the impedance of the stratum corneum of the user, it may be converted into a prescribed current signal and maintained.

The signal detecting unit 200 detects the amount of current from the skin through the current detection electrode 102 and calculates at least one of skin impedance signal and skin admittance signal. Specifically, the signal detecting unit 200 detects the amount and phase of the current through the current detection electrode 102 and converts the current signal into a voltage signal corresponding thereto, and detects at least one of the impedance signal and the admittance signal through the voltage signal converted by using the sinusoidal wave voltage applied to the skin. In addition, the signal detecting unit 200 detects and outputs at least one of an impedance signal and an admittance signal using a voltage signal corresponding to the amount and phase of current detected through the current detection electrode 102 and a sinusoidal wave voltage applied to the skin.

The skin information determination unit 300 analyzes at least one of the impedance signal and the admittance signal from the signal detecting unit 200 to calculate the skin moisture level and the sweat production rate of the user.

Figure 5:
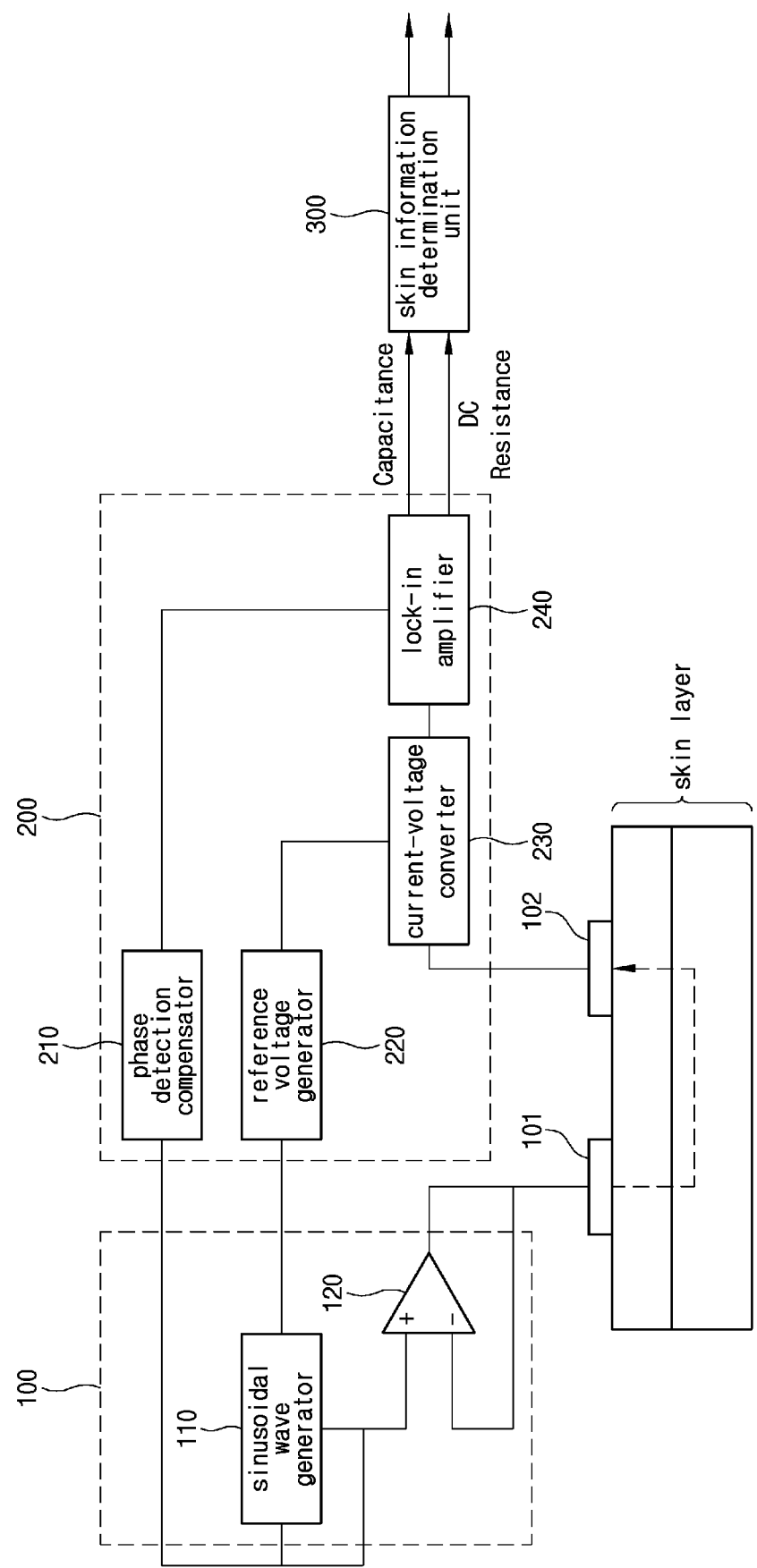
FIG. 5 is a block diagram specifically illustrating the configurations of an electrode driving module and a signal detecting unit of FIG. 4.

FIG. 5 is a block diagram specifically illustrating configurations of an electrode driving module and a signal detecting unit of FIG. 4.

The electrode driving module 100 shown in FIG. 5 includes a sinusoidal wave generator 110 for generating a sinusoidal wave current using a reference voltage to create a voltage having the same phase or an inverted phase with respect to the sinusoidal wave, and an operational amplifier 120 for operationally amplifying the voltage of the same phase or an inverted phase with respect to the sinusoidal wave to apply the sinusoidal wave voltage to the skin of the user through the voltage application electrode 101.

Here, the operational amplifier 120 is configured such that the voltage having the same phase or an inverted phase with respect to the sinusoidal wave is received and operationally amplified to apply the sinusoidal wave voltage to the voltage application electrode 101 at the positive signal input terminal (+). In addition, the operational amplifier 120 is configured such that the sinusoidal wave voltage outputted to an output terminal is feedback and input to the negative signal input terminal (−) thereof. With such a configuration, the operational amplifier 120 may prevent distortion due to skin impedance, thereby improving the accuracy when measuring the skin impedance.

The signal detecting unit 200 is configured to include a reference voltage generator 220, a current-voltage converter 230, a phase detection compensator 210, and a lock-in amplifier 240.

Specifically, the reference voltage generator 220 generates a reference voltage at a predetermined voltage level, and outputs the generated reference voltage to the sinusoidal wave generator 110 and the current-voltage converter 230 of the electrode driving module 100, respectively. The sinusoidal wave generator 110 generates a sinusoidal wave using the reference voltage of a predetermined level as a reference to create a voltage having the same phase or an inverted phase with respect to the sinusoidal wave.

The current-voltage converter 230 receives a reference voltage from the reference voltage generator 220 and detects an amount of current flowing into the stratum corneum from the current detection electrode 102 and then converts the current into a voltage signal corresponding to the detected amount and phase of current of the skin. Here, the amount and phase of current flowing into the stratum corneum and the phase are determined by the impedance component of the contacted skin. The current-voltage converter 230 supplies the converted voltage signal to the lock-in amplifier 240.

The phase detection compensator 210 is connected to the sinusoidal wave generator 110 to detect the phase of the generated sinusoidal wave, compensate phase delay occurring in the detected phase during the signal processing of the current-voltage converter 230 and the lock-in amplifier 240, and provide the phase-compensated sinusoidal to the lock-in amplifier 240.

The lock-in amplifier 240 detects and outputs at least one of the impedance and the admittance from the voltage signal output from the current-voltage converter 230 on a basis of the compensated phase of the sinusoidal wave supplied from the phase detection compensator 210. Specifically, the lock-in amplifier 240 detects only the phase synchronized with the compensated phase of the sinusoidal wave to detect a resistance component of the skin impedance signal or a conductance component of the skin admittance signal, and detects only phase at 90 degrees out of phase from the compensated phase to detect a capacitance component of the skin impedance signal or a susceptance component of the skin admittance signal.

Figure 6:
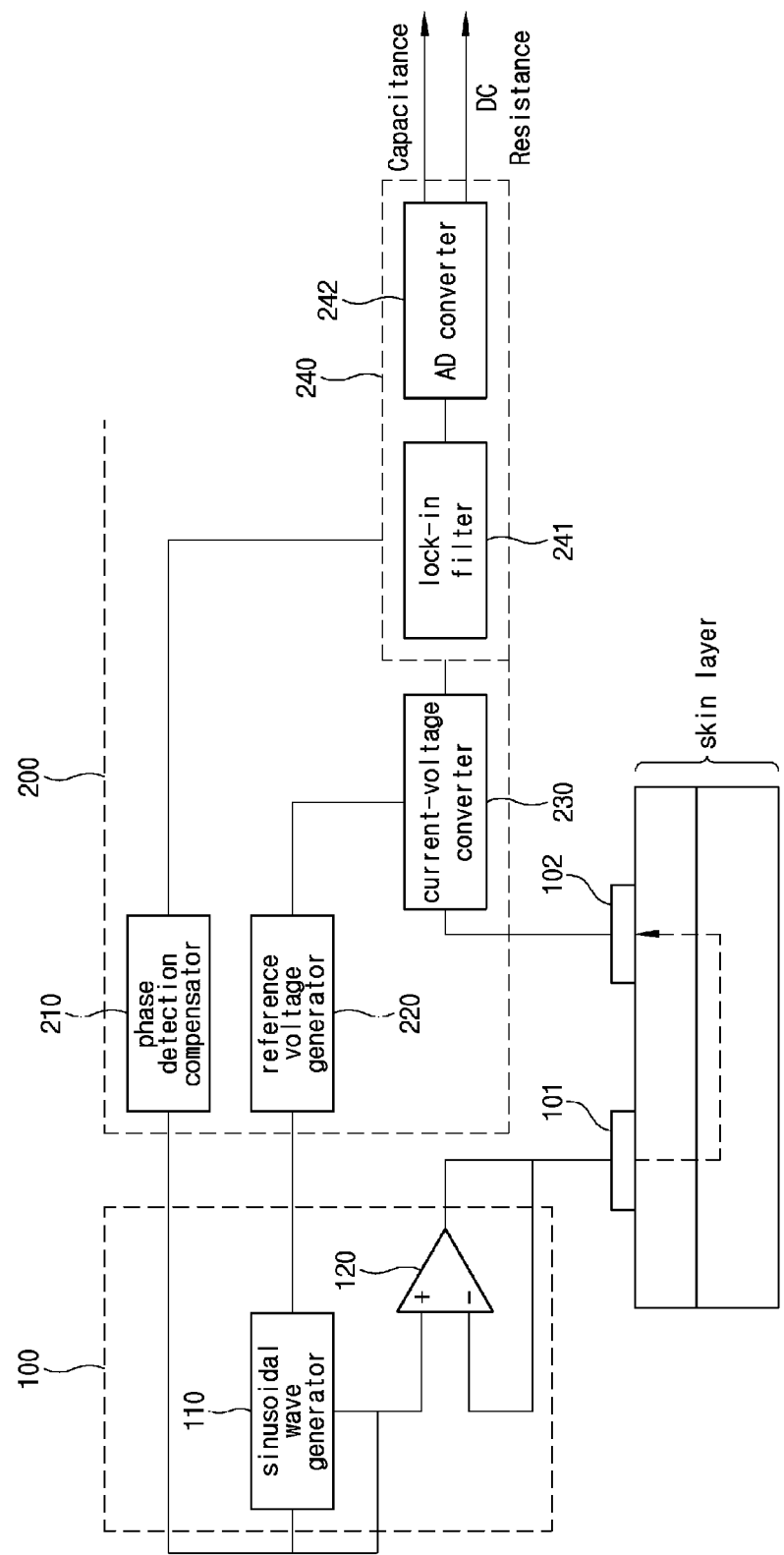
FIG. 6 is a block diagram more specifically showing a configuration including a lock-in amplifier shown in FIG. 5.

FIG. 6 is a block diagram more specifically showing a configuration including a lock-in amplifier shown in FIG. 5.

Figure 7:
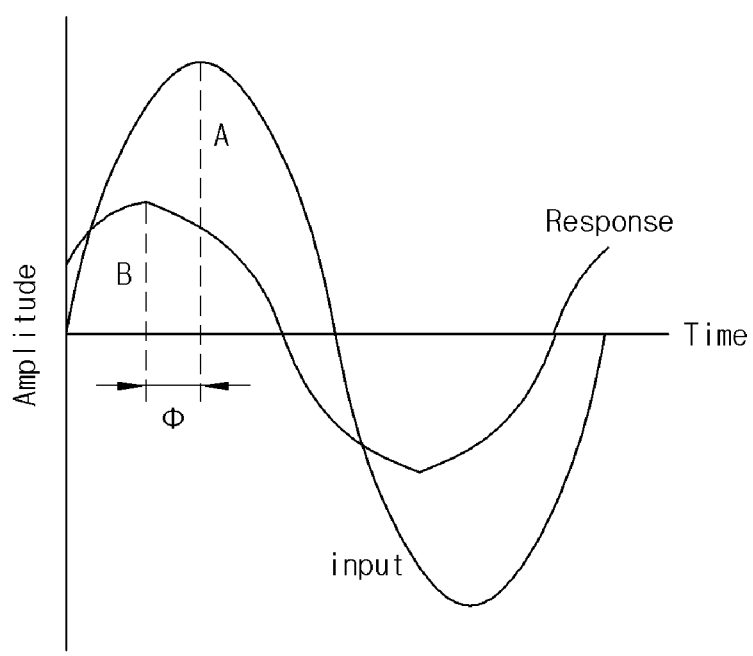
FIG. 7 is a graph showing a current response waveform according to an input of a sinusoidal wave voltage.

The lock-in amplifier 240 shown in FIG. 7 is supplied with the voltage signal output from the current-voltage converter 230 and the sinusoidal wave of the phase compensated through the phase detection compensator 210. The lock-in amplifier 240 is configured to include a lock-in filter 241 for selectively filtering only the components synchronized with the compensated phase of the sinusoidal wave supplied from the phase detector or selectively filtering the components at 90 degrees out of phase from the compensated phase among the voltage signals output from the current-voltage converter and outputting the filtered voltage component as DC voltage waveform, and an AD converter 242 for detecting a voltage value of the filtered DC voltage signal to detect an impedance signal or an admittance signal thereof.

More specifically, the lock-in filter 241 selectively filters only the voltage component synchronized or selectively filters the voltage components at 90 degrees out of phase, with respect to the compensated phase of the sinusoidal wave through the phase detection compensator 210. Then, the lock-in filter 241 supplies the filtered DC voltage waveform to AD converter 242. The AD converter 242 measures and outputs the voltage value of the DC voltage waveform filtered by the lock-in filter.

The method of detecting the impedance signal and the admittance signal of the lock-in amplifier 240 as described above will be described in more detail.

The sinusoidal wave voltage applied to the skin of the user is proportional to the voltage magnitude A in Equation 2 below, and is a sine function obtained by multiplying an angular frequency ω by the time t.

Input: $V_{ac}=A \sin \omega t$ [Equation 2]

The current response from the skin may be represented by Equation 3 below.

Response: $I_{ac}=B \sin(\omega t+\emptyset)$ [Equation 3]

Herein, B is another magnitude and ∅ is a shifted phase angle.

Therefore, the impedance function Z to which Ohm's law is applied may be detected as shown in Equation 4 below.

$$\text{Impedance: } Z = \frac{V_{ac}}{I_{ac}} = \frac{A\sin\omega t}{B\sin(\omega t + \emptyset)}$$ [Equation 4]

FIG. 7 is a graph showing a current response waveform according to an input of the sinusoidal wave voltage.

As shown in FIG. 7, it may be confirmed that the current response waveform is detected in the same manner as the result of expressing the response impedance input by dividing the sine function mathematically into a real part (') and an imaginary part (").

The sine function is divided into the real part (') and the imaginary part ("), and the magnitude (|Z|) of the response impedance may be detected through the impedance function Z using Equations 5 to 9 below.

Input: $V_{ac} = V' + jV''$ [Equation 5]

Response: $I_{ac} = I' + I''$ [Equation 6]

Impedance: $Z = \dfrac{V' + jV''}{I' + jI''} = Z' + jZ''$ [Equation 7]

The magnitude (|Z|) of the response impedance is given by Equation 9 below.

Magnitude: $|Z| = (Z'^2 + Z''^2)^{1/2}$ [Equation 8]

The shifted phase angle Ø shown in FIG. 7 may be detected using Equation 10 below.

Phase angle: $\emptyset = \arctan\dfrac{Z''}{Z'}$ [Equation 9]

Herein, the real part Z' of the impedance function is a response that is in-phase, and the imaginary part Z" of the impedance function is a phase that is out-of-phase.

From an electrical point of view, the impedance function may be represented by a resistance component of a real part and a reactance component of an imaginary part. The lock-in amplifier 240 detects only the phase synchronized with the compensated phase of the DC voltage signal to detect the DC resistance component of the skin impedance signal, and detects only the phase that is 90 degrees out of phase from the compensated phase to detect the reactance component of the skin impedance signal. Since the electrical model of the skin proposed in the technique of the present invention consists of only the resistor and the capacitor, it is noted that the measured reactance component is the same as the capacitance.

The skin measuring apparatus for measuring skin moisture level according to the present invention may be implemented as any one of portable terminals such as a mobile communication terminal, a Personal Digital Assistant (PDA), a portable game machine, an MP3 player, a portable multimedia player (PMP), a digital multimedia broadcasting (DMB), and the like. That is, the skin measuring apparatus for measuring skin moisture level may be implemented as a part of a portable terminal. In addition, the skin measurement device for measuring the skin moisture level may not be implemented as a part of the portable terminal, but may be realized as a single product having an independent configuration.

As described above, the skin measuring apparatus for measuring skin moisture level using the voltage application electrode and the current detecting electrode according to the present invention is capable of accurately analyzing the skin moisture level and the sweat production rate of the user without distortion even with a simple structure, by applying the sinusoidal wave voltage to the user's skin through the voltage application electrode and detecting the amount of current from the skin through the current detection electrode. In particular, it is possible to utilize only a simplified structure by using only two electrodes of the voltage application electrode for applying the sinusoidal wave voltage to the skin and the current detecting electrode for detecting the amount of current flowing through the skin.

Also, since the sinusoidal wave voltage is fed back to the negative input terminal of the operational amplifier which is provided in the electrode driving module to output the sinusoidal wave voltage, distortion due to the skin impedance is prevented so that the accuracy can be improved upon measuring skin impedance. In addition, the accuracy of detection of the impedance or the admittance signal may be further improved by compensating for phase delay occurring in the signal detecting unit that detects the impedance or the admittance signal by sharing and using the sinusoidal wave voltage applied to the skin.

While the present invention has been particularly shown and described with reference to exemplary embodiments thereof, it will be understood by those skilled in the art that various changes and modifications may be made therein without departing from the spirit and scope of the invention as defined by the appended claims. It will be understood that various modifications and changes may be made.

The invention claimed is:

1. A skin measuring apparatus for measuring a skin moisture level, using a voltage application electrode and a current detection electrode, the apparatus comprising:
   an electrode driving module configured to apply a sinusoidal wave voltage to a skin of a user through the voltage application electrode so that an amount of current is output from the skin through the current detection electrode; and
   a signal detecting unit detecting the amount of current from the skin through the current detection electrode to calculate at least one of an impedance signal and an admittance signal;
   wherein the skin measuring apparatus calculates the skin moisture level and a sweat production rate of the user by using the at least one of the impedance signal and the admittance signal; and
   the electrode driving module comprises:
   a sinusoidal generator generating a sinusoidal wave current using a reference voltage to create a voltage having the same phase or an inverted phase with respect to the sinusoidal wave; and
   an operational amplifier configured to operationally amplify the voltage having the same phase or the inverted phase with respect to the sinusoidal wave to apply the sinusoidal wave voltage to the skin of the user through the voltage application electrode.

2. The apparatus according to claim 1, wherein the signal detecting unit detects the amount and phase of the current detected through the current detection electrode and then converts the current into a voltage signal corresponding to the amount of current and phase, and
   detects the at least one of the impedance signal and the admittance signal using the converted voltage signal and a waveform of the sinusoidal wave applied to the skin.

3. The apparatus according to claim 1, wherein the operational amplifier is configured such that the voltage having the same phase or the inverted phase with respect to the sinusoidal wave is received and operationally amplified to apply the sinusoidal wave voltage to the voltage application electrode at a positive signal input terminal (+) thereof; and
   the sinusoidal wave voltage outputted to an output terminal is fed back and input to a negative signal input terminal (−) thereof.

4. The apparatus according to claim 1, wherein the signal detecting unit includes:

a current-voltage converter detecting the amount of current detected from the skin through the current detection electrode and converting the current into a voltage signal corresponding to the amount and phase of current;

a lock-in amplifier detecting and outputting at least one of the impedance signal and the admittance signal from the voltage signal corresponding to the amount and phase of current using a phase of the sinusoidal wave voltage applied to the skin; and a phase detection compensator detecting the phase of the sinusoidal wave applied to the skin and compensating phase delay in the detected phase occurred during signal processing of the current-voltage converter and the lock-in amplifier to provide a phase-compensated sinusoidal wave to the lock-in amplifier.

5. The apparatus according to claim 4, wherein the lock-in amplifier includes:

a lock-in filter receiving the voltage signal output from the current-voltage converter and the phase of the phase-compensated sinusoidal wave, and selectively filtering only the component synchronized or selectively filtering the components at 90 degrees out of phase, with respect to the phase of the compensated sinusoidal wave provided from the phase detection compensator among the voltage signals output from the current-voltage converter, to output a filtered voltage component as a DC voltage waveform; and an AD converter detecting a voltage value of the filtered voltage component as the DC voltage waveform to detect the impedance signal or the admittance signal, respectively.

6. The apparatus according to claim 1, wherein the sinusoidal wave voltage applied to the skin of the user through the electrode driving module is proportional to a voltage magnitude (A) in Equation 2 below, and becomes a sine function obtained by multiplying an angular frequency ($\omega$) by a time (t), and $$\text{Input: } V_{ac} = A \sin \omega t \quad \text{[Equation 2]}$$

the current response from the skin is represented by the Equation 3 below, $$\text{Response: } I_{ac} = B \sin(\omega t + \emptyset) \quad \text{[Equation 3]}$$

where, B is another magnitude and $\emptyset$ is a shifted phase angle.

7. The apparatus according to claim 6, wherein the signal detecting unit detects an impedance function Z to which an Ohm's law is applied through Equation 4 below, $$\text{Impedance: } Z = \frac{V_{ac}}{I_{ac}} = \frac{A \sin \omega t}{B \sin(\omega t + \emptyset)} \quad \text{[Equation 4]}$$

a sine function is divided into a real part (') and an imaginary part (") and a magnitude (|Z|) of a response impedance is detected through the impedance function (Z), using Equations 5 to 9 below, $$\text{Input: } V_{ac} = V' + jV'' \quad \text{[Equation 5]}$$

$$\text{Response: } I_{ac} = I' + I'' \quad \text{[Equation 6]}$$

$$\text{Impedance: } Z = \frac{V' + jV''}{I' + jI''} = Z' + jZ'' \quad \text{[Equation 7]}$$

-continued $$\text{Magnitude: } |Z| = \left(Z'^2 + Z''^2\right)^{1/2}, \quad \text{[Equation 8]}$$

the shifted phase angle ($\emptyset$) is detected using the Equation 10 below, $$\text{Phase angle: } \emptyset = \arctan \frac{Z''}{Z'} \quad \text{[Equation 9]}$$

where, the real part (Z') of the impedance function is a response that is in-phase, and the imaginary part (Z'') of the impedance function is a phase that is out-of-phase.

8. A skin measuring apparatus for measuring a skin moisture level, using a voltage application electrode and a current detection electrode, the apparatus comprising:

an electrode driving module configured to apply a sinusoidal wave voltage to a skin of a user through the voltage application electrode so that an amount of current is output from the skin through the current detection electrode; and a signal detecting unit detecting the amount of current from the skin through the current detection electrode to calculate at least one of an impedance signal and an admittance signal; and wherein the skin measuring apparatus calculates the skin moisture level and a sweat production rate of the user by using the at least one of the impedance signal and the admittance signal;

wherein the signal detecting unit generates a reference voltage at a predefined voltage level and outputting the reference voltage, and the signal detecting unit comprises;

a current-voltage converter configured to detect the amount of current detected from the skin through the current detection electrode and converting the current into a voltage signal corresponding to the amount and phase of current;

a lock-in amplifier detecting and outputting at least one of the impedance signal and the admittance signal from the voltage signal corresponding to the amount and phase of current using a phase of the sinusoidal wave voltage applied to the skin; and a phase detection compensator detecting the phase of the sinusoidal wave applied to the skin and compensating phase delay in the detected phase occurred during signal processing of the current-voltage converter and the lock-in amplifier to provide a phase-compensated sinusoidal wave to the lock-in amplifier; and wherein the lock-in amplifier comprises:

a lock-in filter receiving the voltage signal output from the current-voltage converter and the phase of the phase-compensated sinusoidal wave, and selectively filtering only the component synchronized or selectively filtering the components at 90 degrees out of phase, with respect to the phase of the compensated sinusoidal wave provided from the phase detection compensator among the voltage signals output from the current-voltage converter, to output a filtered voltage component as a DC voltage waveform; and an AD converter detecting a voltage value of the filtered DC voltage component as a DC waveform to detect the impedance signal or the admittance signal, respectively.

* * * * *